United States Patent
McIntosh et al.

(10) Patent No.: US 7,864,972 B2
(45) Date of Patent: Jan. 4, 2011

(54) CUSTOMIZED IN-EAR INTERFACE FOR ACOUSTIC EQUIPMENT AND METHOD

(75) Inventors: Ian McIntosh, Alexandria (CA); Michael C. Turcot, Montréal (CA)

(73) Assignee: Sonomax Hearing Healthcare Inc., Montreal (CA)

( * ) Notice: Subject to any disclaimer, the term of this patent is extended or adjusted under 35 U.S.C. 154(b) by 1030 days.

(21) Appl. No.: 11/250,203

(22) Filed: Oct. 14, 2005

(65) Prior Publication Data

US 2006/0093176 A1 May 4, 2006

Related U.S. Application Data

(60) Provisional application No. 60/618,136, filed on Oct. 14, 2004.

(51) Int. Cl.
*H04R 25/00* (2006.01)
*H04R 25/02* (2006.01)
*H04R 31/00* (2006.01)

(52) U.S. Cl. ............... 381/322; 381/328; 381/324; 181/128; 181/129; 181/130; 29/896.21

(58) Field of Classification Search ............ 381/322, 381/328
See application file for complete search history.

(56) References Cited

U.S. PATENT DOCUMENTS

| 4,800,636 | A | * | 1/1989 | Topholm ............... 29/896.21 |
| 4,962,537 | A | * | 10/1990 | Basel et al. .............. 381/324 |
| 5,006,055 | A | * | 4/1991 | Lebisch et al. ............ 425/2 |
| 5,957,136 | A | * | 9/1999 | Magidson et al. .......... 128/864 |
| 6,339,648 | B1 | | 1/2002 | McIntosh et al. |
| 6,687,377 | B2 | | 2/2004 | Voix et al. |
| 6,754,357 | B2 | * | 6/2004 | McIntosh et al. .......... 381/322 |
| 6,768,803 | B1 | | 7/2004 | Duhamel |

OTHER PUBLICATIONS

PCT International Search Report; International Application No. PCT/CA2005/001594; Sonomax Hearing Healthcare Inc. et al.

* cited by examiner

*Primary Examiner*—Brian Ensey
*Assistant Examiner*—Sunita Joshi
(74) *Attorney, Agent, or Firm*—Carter, Schnedler & Warnock

(57) ABSTRACT

An in-ear interface comprises an ear module shaped to be received in an ear canal. The ear module has a core defining a sound bore for enabling sound transmittance into the ear canal. A sheath covers a portion of an outer surface of the core so as to define an expandable space between the sheath and the core. An opening is defined in the core communicating with the expandable space whereby the expandable space is adapted to receive a settable compound to expand the ear module to the shape of the ear canal. An insert is secured to the ear module and has a slender portion received at least partially in the sound bore to generally maintain a shape of the sound bore during reception and curing of the settable compound in the expandable space.

18 Claims, 5 Drawing Sheets

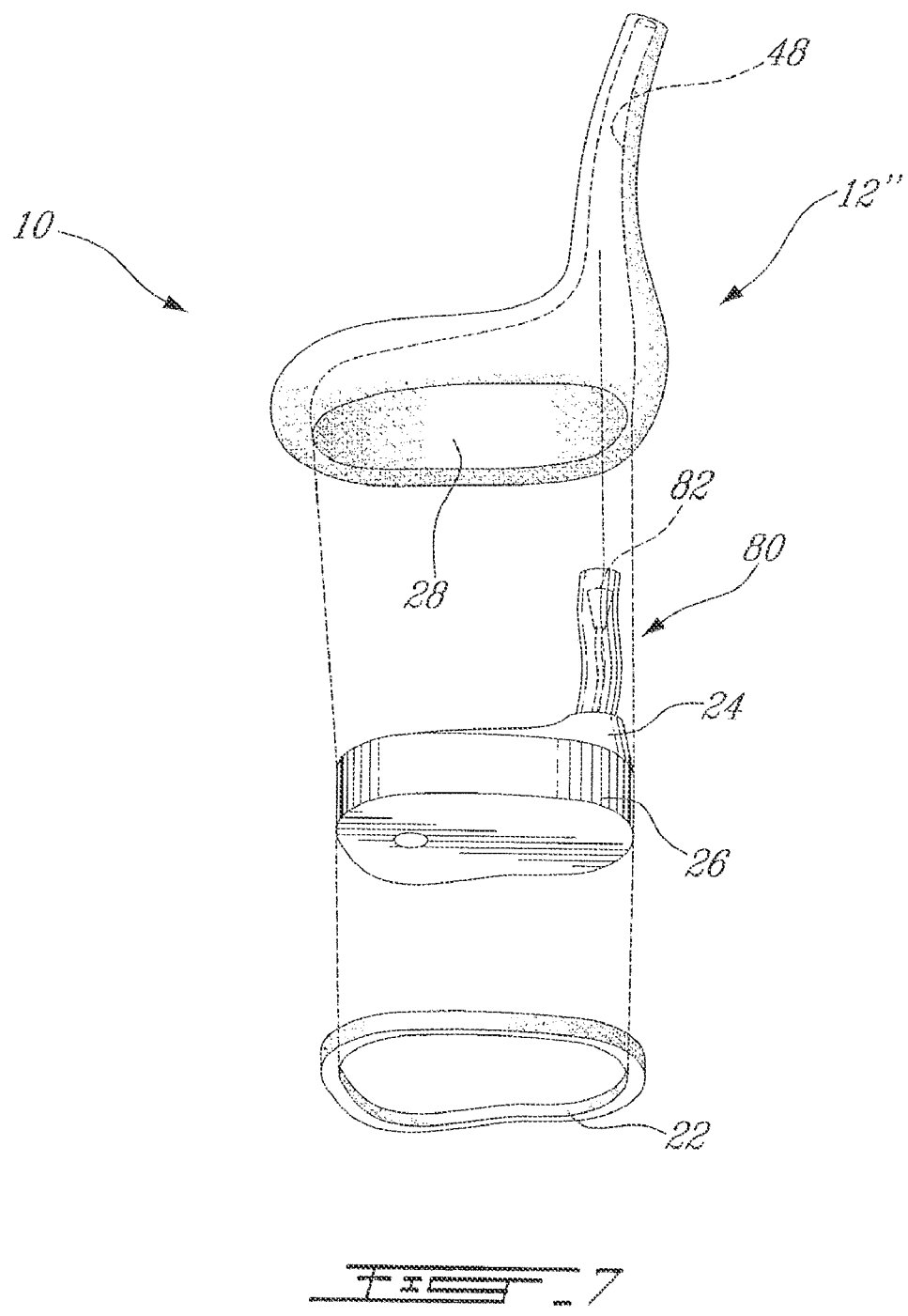

CUSTOMIZED IN-EAR INTERFACE FOR ACOUSTIC EQUIPMENT AND METHOD

CROSS-REFERENCE TO RELATED APPLICATION

The present patent application claims priority on U.S. Provisional Patent Application No. 60/618,136, filed on Oct. 14, 2004, by the present applicants.

BACKGROUND OF THE INVENTION

1. Field of the Invention

The present invention relates to in-ear devices such as hearing-aid devices, sound filter earplugs and the like, and more particularly to a customized in-ear interface for supporting acoustic equipment in an ear and a method for producing same.

2. Background Art

In-ear interfaces of many different types are found in various applications. Essentially, in-ear interfaces (also known as in-the-ear devices) are received in the ear canal so as to transmit or block selected sound/noise through selected acoustic equipment/electronics, such as microphones, receivers, speakers, micro-controllers and associated components. For instance, in-ear interfaces are part of hearing-aid devices, earplugs, headsets, audio transmitters, amongst other devices. With the high demand for in-ear interfaces, customized in-ear interfaces (i.e., custom-shaped to an ear canal) have been developed to specifically suit consumers.

A few design factors are to be considered in designing and fabricating customized in-ear interfaces. The in-ear interface must generally match a portion of the geometry of the ear canal, so as to be efficient in transmitting/blocking sound, as well as be comfortable to wear. Also, the time and costs involved in producing customized in-ear interfaces is also an important design factor.

Presently, customized in-ear interfaces are made of rigid materials, such as acrylic. As a result, a non-negligible amount of customized in-ear interfaces are rejected by recipients claiming the product to be too uncomfortable to wear.

Customized in-ear interfaces, as described previously, are fabricated according to a lengthy process that spans over at least a few days, if not weeks. The process involves the creation of a personalized plaster ear-canal model, followed by a multi-step reproduction of the model, which is done off site. Accordingly, a delay results from these steps between the on-site model creation, and the reception and distribution of the end product to the consumer. This also excludes the potential rejection by the consumer for lack of comfort of the in-ear interface or inefficient fit, which rejection adds to the delay in reception of an end product by the consumer.

Inefficient fitting of an in-ear interface results in the occurrence of feedback with present-day customized in-ear hearing aids. These issues explain why present-day customized in-ear interfaces are costly.

SUMMARY OF INVENTION

Therefore, an object of the present invention is to provide a novel customized in-ear interface for acoustic equipment.

It is another object of the present invention to provide a customized in-ear interface and method of producing same that substantially overcome the disadvantages of the prior art.

Another object of the present invention is to provide a customized in-ear interface for a hearing aid and method of production that enables a customer to be fitted for the hearing aid in situ.

Therefore, in accordance with the present invention, there is provided an in-ear interface, comprising: an ear module shaped to be at least partially received in an ear canal, the ear module having a core defining a sound bore for enabling sound transmittance into the ear canal, a sheath covering a portion of an outer surface of the core so as to define an expandable space between the sheath and the core, and an opening defined in the core communicating with the expandable space whereby the expandable space is adapted to receive a settable compound to expand the ear module to the shape of the ear canal; and an insert secured to the ear module and having a slender portion received at least partially in the sound bore to generally maintain a shape of the sound bore during reception and curing of the settable compound in the expandable space.

Further in accordance with the present invention, there is provided a method for customizing an in-ear interface in an ear of a person, comprising the steps of: providing an ear module having an expandable body defining a cavity; inserting at least partially an insert in the cavity of the ear module to generally maintain the shape of the cavity; inserting the ear module in an ear of the person; injecting a settable compound in the expandable body such that the ear module generally takes the shape of the ear; removing the insert from the ear module upon curing of the settable compound so as to liberate the cavity of the ear module; and inserting acoustic equipment in the cavity of the ear module such that the equipment can transmit sound to the ear through the in-ear interface.

BRIEF DESCRIPTION OF THE DRAWINGS

Having thus generally described the nature of the invention, reference will now be made to the accompanying drawings, showing by way of illustration a preferred embodiment thereof and in which:

FIG. 7 is an exploded view of the in-ear interface in accordance with another embodiment.

DESCRIPTION OF THE PREFERRED EMBODIMENTS

Figure 1:
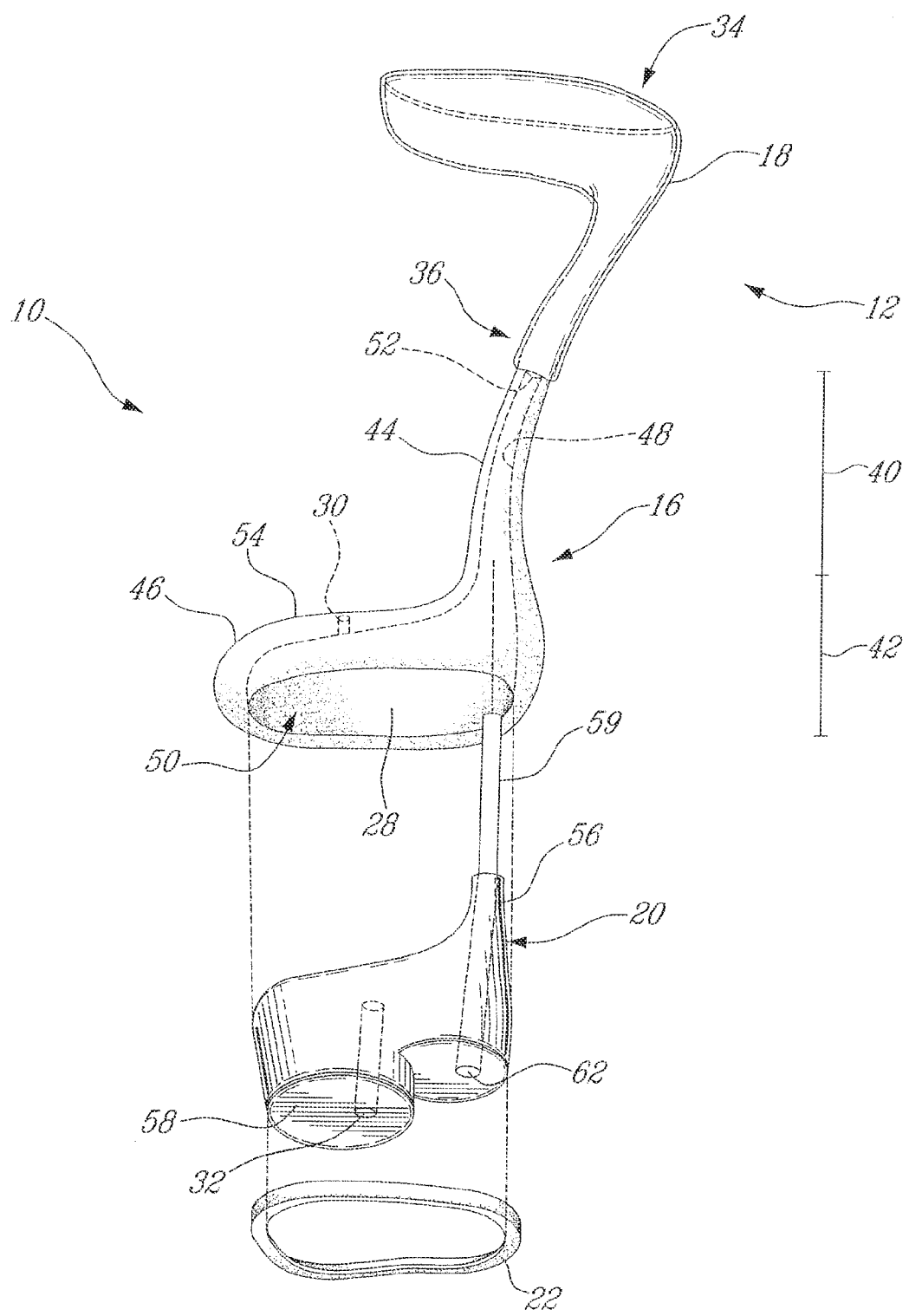
FIG. 1 is an exploded view of an ear module of an in-ear interface in accordance with a preferred embodiment of the present invention, prior to pre-fitting production and in relation to an insert and retainer ring.

Referring to FIG. 1, there is shown an embodiment of an in-ear interface 10 for adapting acoustic equipment to an ear, for sound transmission or attenuation. According to a preferred embodiment, the in-ear interface 10 will be customized for customers following a sequence of steps described hereinafter, whereby it will be referred to hereinafter as "customized in-ear interface 10" notwithstanding the customizing phase at which the interface 10 is. The in-ear interface 10 consists of an expandable ear module 12 that is custom-fitted to an ear. The in-ear interface 10 also has various supporting components that are adapted for interaction with the ear module 12 and/or the acoustic equipment, to make the final product.

Figure 5:
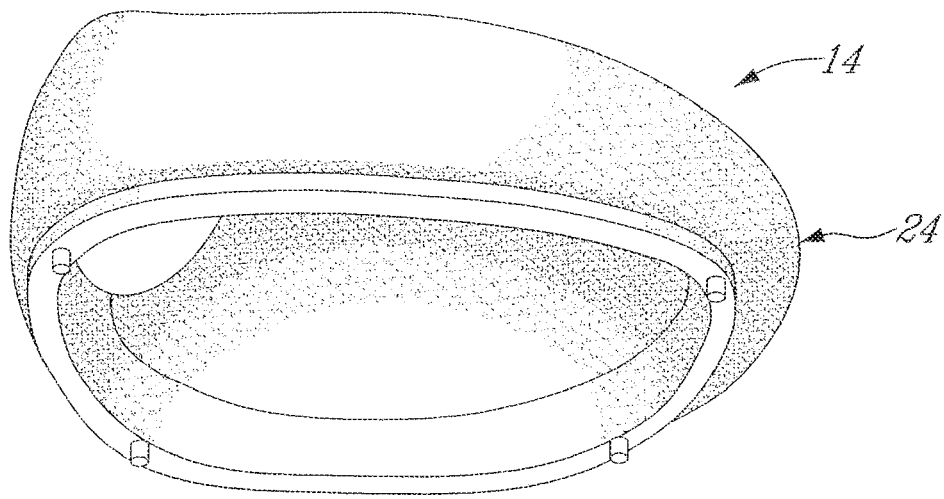
FIG. 5 is a perspective view of a shell of the in-ear interface.
Figure 6:
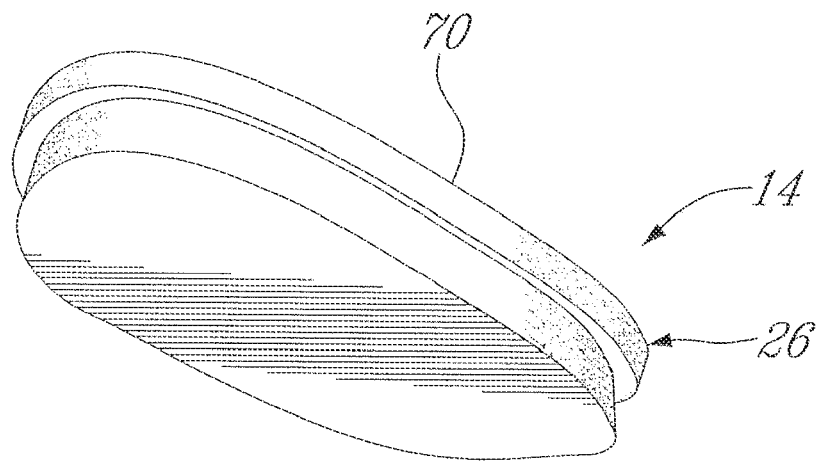
FIG. 6 is a perspective view of a face plate of the in-ear interface.

Referring to FIG. 1, the expandable ear module 12 is shown prior to being configured for customizing. The expandable ear module 12 is made up of a core 16 (e.g., a flexible core) with an integral stretchable sheath 18. According to one embodiment, the supporting components include an insert 20, a retainer ring 22, a shell 24 and a face plate 26 (FIGS. 5 and 6).

The method of customizing the in-ear interface 10 for a customer is generally made up of three phases. The first phase is the pre-fitting phase consisting of the assembly of the expandable ear module 12 with use of some of the supporting components, such as the insert 20 and retainer ring 22 or adhesive, so as to bring the ear module 12 from its initial configuration, illustrated at 12 in FIG. 1, to a customizing-ready configuration, illustrated at 12' in FIG. 2.

The second phase is the fitting phase whereby the expandable ear module 12' (as in FIG. 2) in interaction with the insert 20 and retainer ring 22 is customized to fit a customer's ear.

The third phase is the post-fitting phase whereby some of the supporting components, as well as acoustic equipment, are added to the ear module 12' to yield a final product.

Pre-Fitting Phase

Figure 2:
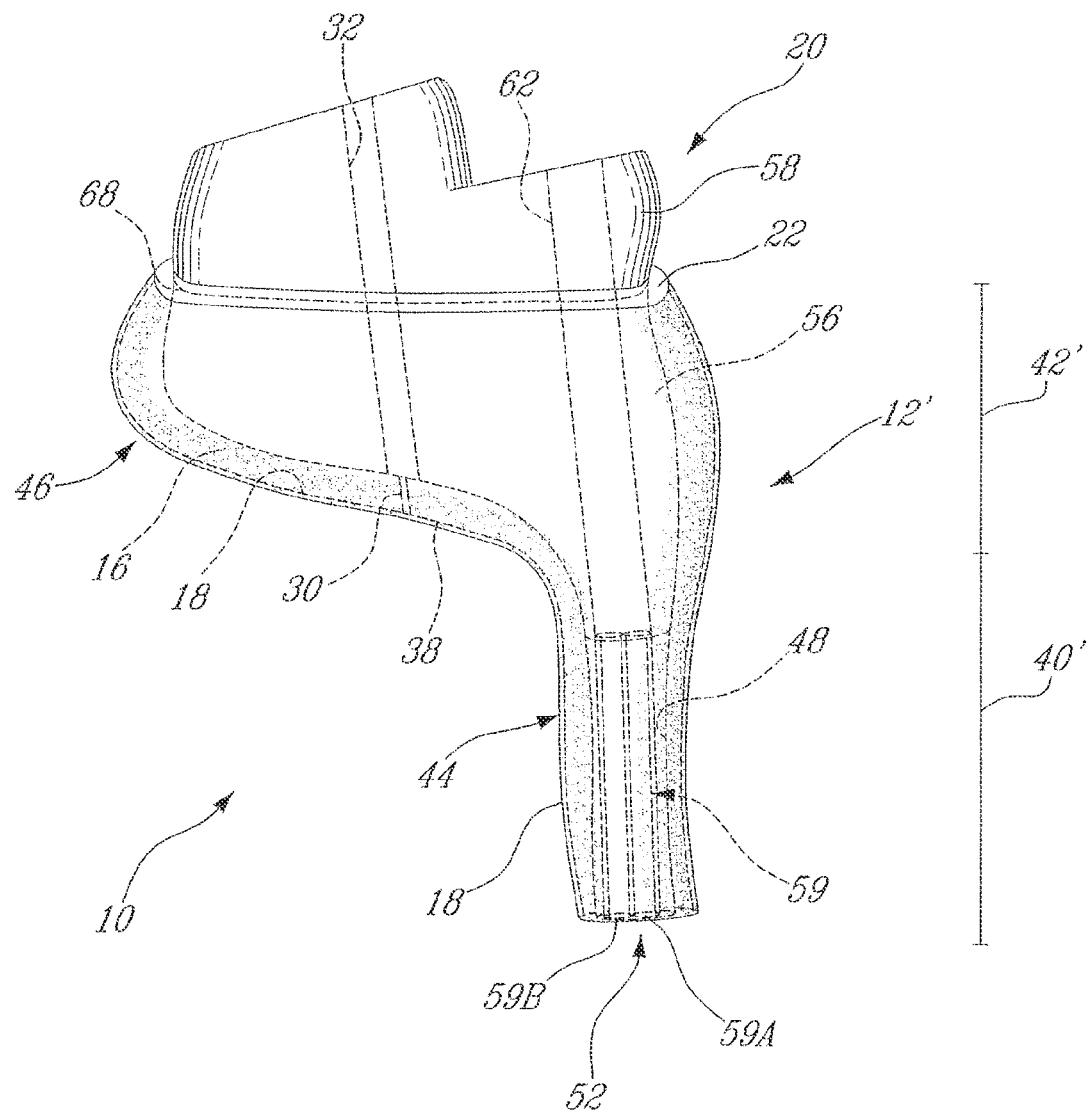
FIG. 2 is a perspective view of the ear module before fitting, with insert and retainer ring in place.
Figure 3:
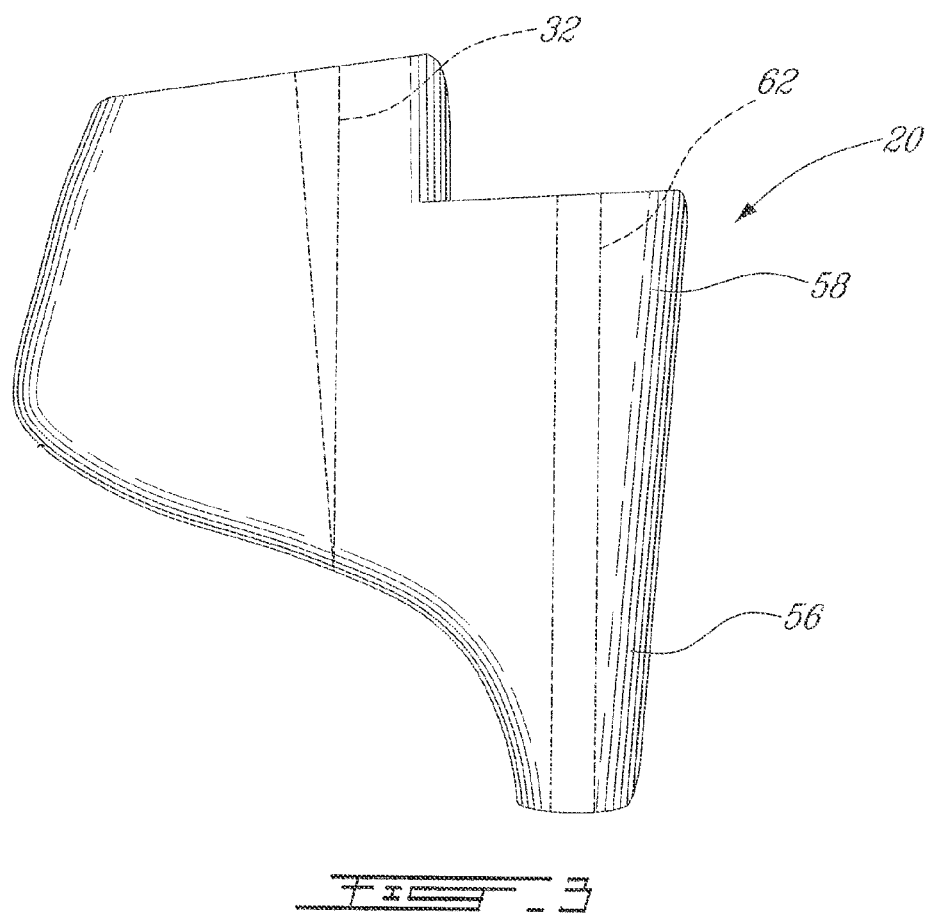
FIG. 3 is a perspective view of the insert.

Now referring more specifically to FIG. 1, shown is an exploded view of the expandable ear module 12 before assembly in interaction with the insert 20 as required for the pre-fitting phase. The first phase consists of initially inserting the insert 20 in a cavity 28 in the core 16. The insert 20, as best seen in FIG. 3, is adapted to fit snugly within the cavity 28 of the core 16 while protruding therefrom. The insert 20 provides structural support to the expandable ear module 12 (and as configured at 12' in FIG. 2) throughout the pre-fitting and fitting phases.

Figure 4:
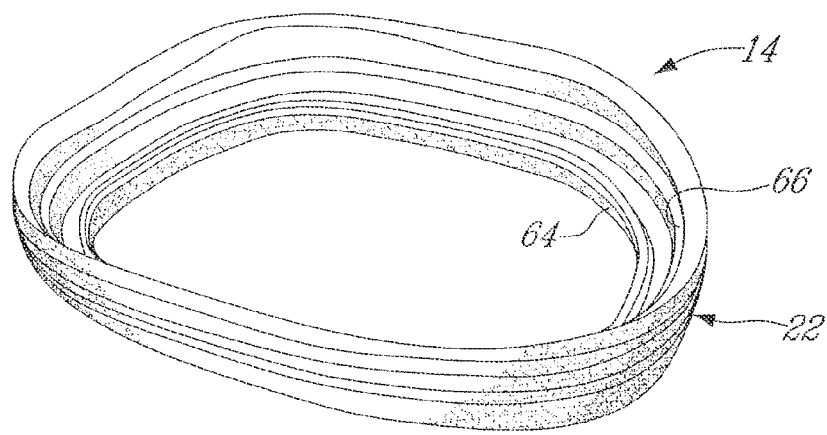
FIG. 4 is a perspective view of the retainer ring.

In order to ensure that the core 16 remains in position over the insert 20, the retainer ring 22, as depicted individually in FIG. 4, is optionally used as additional structural support. Therefore, the retainer ring 22 is attached onto the core 16 that is engaged with the insert 20, so that the core 16 and the insert 20 are held in place relative to one another, as shown in FIG. 2. Adhesives could alternatively be used to ensure that the core 16 and the insert 20 are secured to one another.

Then, the sheath 18, having a free end 34 and a connected end 36 by which the sheath 18 is connected to the core 16, is preferably folded inside out over the core 16 at the connected end 36. As shown concurrently in FIGS. 1 and 2, the sheath 18 is folded in this embodiment such that the free end 34 overlays the core 16 adjacent to the insert 20 and the retainer ring 22. Subsequently, the free end 34 of the sheath 18 is secured (e.g., glued) to the core 16, whereby an expandable space 38 is defined between the core 16 and the sheath 18. This will result in the ear module 12 reaching its customizing-ready configuration illustrated as 12' in FIG. 2. It is pointed out that the sheath 18 may be folded over the core 16 in this embodiment prior to the insertion of the insert 20. The expandable space 38 (FIG. 2) will expand on receiving a settable compound therein, when the ear module 12 is custom-fitted to the ear canal of a customer, as will be described hereinafter.

An aperture must be provided in the core 16 for the injection of a settable compound into the expandable space 38. Accordingly, the core 16 may be molded with such an aperture. Alternatively, a slit 30 may be punched through the core 16 prior to the sheath 18 being folded thereon. For instance, a tool may be provided so as to be inserted through an aperture 32 in the insert 20 to punch the slit 30. Another aperture, such as sound bore 62, is typically provided so as to be used for the support of the core 16 by the tool during the punching of the aperture 32. The pre-fitting phase is thus essentially completed.

However, optional steps may be performed in this phase. For instance, once the sheath 18 is secured to the core 16, the pre-fitting in-ear interface 10 may be surface treated or tested for waterproofness, to ensure that the sheath 18 can withstand the injection of a settable compound in the fitting phase. Surface treatment is performed to increase the lubricity of the sheath 18 and to ensure a smooth surface finish for easy insertion of the ear module 12' in the ear canal.

The in-ear interface 10 as shown in FIG. 2 may then be tested for waterproofness. Particularly, the sheath 18 is inspected for rips and for possible improper application of glue to its free end 34, which could potentially leave a portion of the free end 34 unsecured to the core 16. Thus, the expandable space 38 would not be sealed off. A possible inspection technique to test for the above mentioned imperfections consists of injecting air (e.g., using a syringe through the slit 30 and the aperture 32) into the expandable space 38 and placing the in-ear interface 10 in water for leak verification. Other techniques to test waterproofness can also be used.

Fitting Phase

The second phase, or fitting phase of the customized in-ear interface 10, is carried out efficiently on site. It is in this phase that the ear module 12' shown in FIG. 2 is shaped to the ear of the customer. More specifically, the ear module 12' comprises a proximal portion 40' adapted for insertion in the ear canal and a distal portion 42' adapted for placement in the concha region of the ear. Once the slender proximal portion 40' has been inserted in the ear canal, the distal portion 42' containing the insert 20 is manipulated to obtain proper placement of the ear module 12' with respect to the concha region. It is pointed out that the proximal portion 40' and the distal portion 42', as illustrated in FIG. 2, are the same as those illustrated at 40 and 42 in FIG. 2, with the sheath 18 flipped on the ear module 12' in FIG. 2.

Then, to customize the ear module 12', a fast-curing compound is injected into the expandable space 38 between the core 16 and the sheath 18, for instance, via a syringe inserted through the aperture 32 of the insert 20 and slit 30 of the core 16. The injected material forces the sheath 18 to expand and take the actual form of the ear canal and concha region of the customer being fitted. The ear module 12' is expanded until a comfortable fit and an acoustic seal is achieved.

At this point, a waiting period is required for the injected material to cure leaving the ear module 12' permanently shaped to the customer's ear. Following the waiting period, the in-ear interface 10 is ready for the post-fitting phase. Effectiveness of the acoustic seal can be verified by using the sound bore provided for in the design. The method and apparatus described in U.S. Pat. No. 6,687,377 can be used for this purpose.

Post-Fitting Phase

The third-phase, or post-fitting phase, consists of adding some of the supporting components to complete the customized in-ear interface 10, such that the in-ear interface 10 can accommodate acoustic equipment. According to one embodiment, during post-fitting, the retainer ring 22 (if used) and the insert 20 are removed from the expanded ear module 12'. The insert 20 is removed if it is to be replaced by acoustic equipment, whether passive or active. In such a case, the insert 20 has been used to provide structural support for the cavity 28 and/or sound bore 48 of the core 16 to maintain their respective shape during the pre-fitting and the fitting phases.

The insert 20 can alternatively be used to support acoustic equipment, in which case the insert 20 remains assembled with the core 16. Acoustic equipment is then mounted onto the insert 20, as will be described hereinafter.

According to one embodiment, the shell 24 and face plate 26 illustrated in FIGS. 5 and 6 respectively, are utilized as a means of containment for the acoustic equipment in the ear module 12'. The shell 24 is adapted to receive the face plate 26 such that a tight seal is formed therebetween. The shell 24 is adapted to fit snugly within the cavity 28 of the distal portion 42' of the expanded ear module 12', which has taken the shape of the insert 20. Notably, the face plate 26 can be attached to the shell 24 either before or after it is inserted in the ear module 12'. For instance, the face plate 26 may support electronic components and be fixed to the shell 24, in which case the shell 24/face plate 26 is connected as a whole to the expanded ear module 12'. In such a case, access is preferably provided in the face plate 26 such that a battery, a customized chip or the like may be received in the shell 24.

The retainer ring 22 depicted in FIG. 4 is once again attached onto the core 16 that is now engaged with the shell 24 so that the core 16 and the shell 24 are held in place relative to one another. Once again, an adhesive may be used as an alternative to the retainer ring 22. The acoustic equipment may be installed in the shell 24 before or after the shell 24 is fitted in the cavity 28. The in-ear interface 10 is then ready for use.

Referring to FIG. 7, the ear module is shown at 12", having been customized for a user person. The shell 24/face plate 26 combination is shown having a sleeve 80 accommodating a receiver 82 connected to the hearing electronics of the shell 24/face plate 26. The sleeve 80, extending beyond the receiver 82 lengthwise, is typically used to position the receiver 82 within the sound bore 48 of the ear module 12". Once the receiver 82 is suitably positioned within the sound bore 48, the exceeding portion of the sleeve 80 may be cut away, or connected to an end of the sound bore 48. It is pointed out that the sleeve 80/receiver 82 assembly preferably forms a flexible link with the shell 24. The flexible link between the sleeve 80/receiver 82 assembly and the shell 24 facilitates the alignment with respect to the formed angle of the cavity 28.

Now with reference to all the annexed drawings, the embodiments as made reference to in the method of producing a customized in-ear interface 10 will be further described in detail.

Ear Module 12/12'

With reference to FIG. 1, the expandable ear module 12', adapted for comfortable placement in the ear canal and concha region of the ear, comprises the core 16 with the integral stretchable sheath 18. The proximal portion 40 has a slender tube 44, whereas the distal portion 42 has a curved base 46. The curved base 46 has the cavity 28 previously mentioned.

The cavity 28 is generally the same shape as the curved base 46 and extends into a sound bore 48 through the slender tube 44 of the core 16. Thus, the cavity 28 with the sound bore 48 extension acts as a means for conducting sound from a source outside the ear canal to inside the ear canal. More specifically, the sound bore 48 opens to an open end 52 of the slender tube 44, opposing an opening 50 of the cavity 28.

Furthermore, the stretchable sheath 18, having a free end 34 and a connected end 36 as previously described, is preferably integrally connected to the slender tube 44 adjacent to the open end 52. For instance, the core 16 and the sheath 18 can be integrally molded to one another, or bonded from two distinct parts.

As shown in FIG. 1, the sheath 18 is shaped such that it covers the core 16 once positioned thereon. The sheath 18 acts as a means of altering the shape and size of the ear module 12 upon fitting. Specifically, when the sheath 18 is positioned over the core 16, it acts as an outer layer in the same form as the core 16, that defines together with the core 16 the expandable space 38 (FIG. 2). More specifically, by securing the free end 34 of the sheath 18 to the base 46 of the core 16, as described previously, the expandable space 38 (FIG. 2) of variable size is created therebetween. Distinctively, the free end 34 is secured to the base 46 adjacent to the opening 50 of the cavity 28 as shown in FIG. 2. Whether the sheath 18 and the core 16 are integrally molded or bonded from two distinct parts, loose end(s) of the sheath 18 is/are glued to the core 16 to seal off the expandable space 38.

Furthermore, the expandable space 38 (FIG. 2) is accessible by way of the slit 30 created during the pre-fitting phase of production. The slit 30 receives a syringe therethrough as is suggested by the above-described method of production. A preferred embodiment of the invention describes the slit 30 as being punched through a surface 54 (FIG. 1) of the base 46 opposing the opening 50 (FIG. 1) of the cavity 28 in the core 16, whereby the slit 30 is aligned with the cavity 32 of the insert 20. However, alternative slit locations are also possible under the present method. It is pointed out that a small flat slit 30 would seal itself off by the resilience of the core 16 and this flat shape of the slit 30.

The thickness of the material of the sheath 18 is to be considered in order to ensure a desired distribution of the settable compound in the expandable space 38, so as to match the shape of the ear. The thickness is to be selected with respect to the evaluated pressure of settable compound during injection thereof in the expandable space. For instance, a thickness range of 0.20 to 0.25 mm is well suited. Specific locations on the sheath 18 have thicknesses in excess of this range in order to delay inflation in desired areas.

Although the ear module 12 is described as a single integral component, it is also contemplated to provide the ear module 12 in a plurality of components. For instance, the ear module 12 may have an ear canal member, and a cavum concha member, separate from one another.

Insert 20

Now referring to FIG. 3, the insert 20 is a supporting component designed to uphold the core 16 during the first and second phase of production. More specifically, the insert 20 adds structural integrity to the core 16 which would otherwise potentially collapse when injected with the molding compound. Therefore, the insert 20 is shaped to be accommodated in the cavity 28 and in a portion of the tubular sound bore 48. The insert 20 has an insertable portion 56 and a protruding portion 58. In one embodiment, the protruding portion 58 acts as a means of attachment for the retainer ring 22 (if used), or as a bonding surface, such that the relative position between the ear module 12 (and 12') and the insert 20 is generally fixed.

The insert 20 may alternatively serve as support for acoustic equipment, whether passive or active. In such a case, the sound bore 62 of the insert 20 will be used to transmit sound to the ear.

It is considered to have an extension of the insert 20 received in the tubular sound bore 48 of the ear module 12'/12". In one embodiment, the insert 20 has a tubular portion 59 mounted at an end of the insertable portion 56. The tubular portion 59 is preferably a stiff tube with a controlled level of flexibility, that will help maintain the structural integrity of the sound bore 48 of the ear module 12 during the post-fitting and fitting phases.

The tubular portion 59 is typically flexible with respect to a remainder of the insert 20, so as to facilitate its insertion in the sound bore 48 of the ear module 12. Moreover, when the ear module 12'/12" is positioned in the ear of the user, the relative movement between the tubular portion 59 and the remainder of the insert 20 permits alignment of the ear module 12'/12" in the ear.

The tubular portion 59 may have multiple channels (e.g., channels 59A, 59B), such that different channels can be used for different uses. For instance, channels of the tubular portion 59 can be used for sound transmission, for pressure relief in view of a pressure differential at the in-ear interface, and/or for defining a measurement port.

Moreover, the insert 20 enables the ear module 12 to be manipulated for pre-fitting production. For instance, the ear module 12 can be held immobile during slit 30 punching and sheath 18 securing by way of the protruding portion 58 of the insert 20, which has the sound bore 62 by which the ear module 12 may be supported. The sound bore 62 facilitates attachment of the ear module 12 to the tools employed during the first phase of production.

The aperture 32 extends through the body of the insert 20 so as to yield a passageway for a slit punching tool and syringe.

It is pointed out that the insert 20 may advantageously be made of a soft (i.e., resilient, deformable) resilient material. More precisely, the geometries of the ear canal and of the concha region of the ear are specific to each person. Accordingly, the insert 20, and especially its tubular portion received in the sound bore 48, must not impede on the deformation of the ear module 12' when the latter is fitted in the ear canal. Accordingly, providing the insert 20 in a soft deformable material allows the adaptation of the ear module 12' to the ear canal of each person.

The insert 20 may also be used as a platform for supporting hearing electronic equipment. For example, the insert 20' can be preformed to subsequently support hearing electronic equipment. Additional ones of the sound bore 62 could be provided, for instance to create a feedback loop for testing/adjustment purposes. In such an embodiment, the insert 20 is typically glued into the ear module 12, so as to be permanently fixed thereto. It is also contemplated to use the combination of the ear module 12' and insert 20 as an earplug.

Retainer Ring 22

Referring now to FIG. 4, the retainer ring 22 has an annular body with an inner rim surface 64 and outer rim surface 66 for simultaneous interaction with the ear module 12' and the insert 20 during the previously described steps. The inner rim surface 64 of the retainer ring 22 is sized as a function of the dimension of the protruding portion 58 of the insert 20 or of the shell 24 and face plate 26, whereas the outer rim surface 66 is sized as a function of the size of the core 16 at the opening 50 of the cavity 28. An adhesive joint is typically formed between the ear module 12' and the insert 20, which adhesive joint 20 is pressured thereafter by the retainer ring 22.

As best shown in FIG. 2, the retainer ring 22 is designed to be mounted tightly over the intersection 68 between the ear module 12' and the insert 20. In the finished in-ear interface 10, the retainer ring 22 will be mounted tightly over the intersection 68 between the ear module 12' and the face plate 16 in order to anchor one to the other. Therefore, the retainer ring 22 will ensure that the relative position between the ear module 12 (i.e., 12') and the insert 20/shell 24 remains generally fixed.

To ensure a tight fit, the retainer ring 22 may consist of an elastic material.

Acoustic Equipment

As depicted in FIGS. 5 and 6 respectively, the shell 24 and face plate 26 are provided to support the acoustic equipment into the customized in-ear interface 10.

In the case of a hearing aid, such electronics consist of a battery, a volume control button, a microphone, a speaker (i.e., receiver), and a configurable electronic chip. The shell 24 is adapted to accommodate the listed electronic components within its concave structure. As previously stated, the shell 24 generally has the same geometry as the insert 20 such that, upon removal of the insert 20 once the compound has cured at fitting, the cavity 28 is adapted to accommodate the shell 24. The face plate 26 attaches flush to a portion of the shell 24 protruding from the cavity 28.

Alternatively, the shell 24 can be designed to fit entirely within the cavity 28 of the core 16; hence, the retainer ring 22 would then grasp onto the face plate 26 protruding from the cavity 28 and not the shell 24.

Moreover, the face plate 26 (FIG. 6) is designed to have a flat surface of attachment 70 of the same diameter and thickness as the flat surface of attachment 72 of the shell 24. Therefore, a tight seal between the two components is formed. In this embodiment, since the face plate 26 is the component that is furthest away from the ear canal once the hearing aid has been inserted in the ear, it is preferably designed with a hinged door for battery access and an aperture for receiving the volume control button therethrough. Thus, the button is exposed and can be adjusted by the user without removing the face plate.

It is contemplated to fit the receiver/speaker of electronic equipment out of the shell 24 and in a portion of the sound bore 48 (FIG. 2). Such a configuration would enable the optimization of sound transmission, as the receiver/speaker would be positioned so as to comply with canal configuration.

The acoustic equipment may be passive, such as plugs received in the cavity 28 of the ear module 12, or active, as discussed previously. In one embodiment, filtering electronics are used with the insert 20 or in the cavity 28, so as to receive ambient noise, and transmit selected sounds through the in-ear interface to the ear canal.

It is also contemplated to use the cavity 28 as a support platform for other equipment, whether directly or indirectly, such as a wireless receiver receiving audio signals from a portable transmitter carried by the customer. Therefore, the in-ear interface 10 essentially represents a support for various types of acoustic equipment/electronics, which is customized to the ear of the customer, and which acts as a plug to substantially prevent undesired sound/noise to be transmitted to the ear canal.

Although the present customized in-ear interface and method of production has been described with a certain degree of particularity, it is to be understood that the disclosure has been made by way of example only and that the present invention is not limited to the features of the embodiments described and illustrated herein, but includes all variations and modifications within the scope and spirits of the invention as hereinafter claimed.

The invention claimed is:

1. An in-ear interface, comprising:
an ear module made of a non-rigid material and shaped to be at least partially received in an ear canal, the ear module having:
a core made of a deformable material and defining a cavity and a sound bore for enabling sound transmittance into the ear canal;

a sheath covering a portion of an outer surface of the core so as to define an expandable space between the sheath and the core; and an opening defined in the core communicating with the expandable space whereby the expandable space is adapted to receive a settable compound to expand the ear module to the shape of the ear canal; and an insert secured to the ear module and having a slender portion sized to extend substantially into the sound bore, and a base portion of the insert received at least partially in the cavity, the insert being made of a non-rigid material deformable concurrently with the core when the ear module is inserted in the ear canal while the slender portion is in the sound bore to generally maintain a shape of the sound bore during insertion into the ear canal, reception and curing of the settable compound in the expandable space, the slender portion being bendable relative to the base portion of the insert to facilitate insertion thereof into the sound bore.

2. The in-ear interface defined in claim 1, wherein the slender portion of the insert is received through the entire sound bore to maintain a diameter of the sound bore during reception and curing of the settable compound in the expandable space.

3. The in-ear interface defined in claim 2, wherein the slender portion of the insert has selected stiffness and flexibility.

4. The in-ear interface defined in claim 2, wherein the slender portion is a tubular member extending from the base portion of the insert.

5. The in-ear interface defined in claim 4, wherein the slender portion has multiple canals for communication, measurement and venting with the ear canal through the sound bore.

6. The in-ear interface defined in claim 1, wherein the sound bore intersects with the cavity.

7. The in-ear interface defined in claim 1, wherein the base portion defines the cavity and the slender portion extending from the base portion defines the sound bore, the slender portion is adapted for insertion in the ear canal of an ear and the base portion is adapted for placement in a cavum concha of the ear.

8. The in-ear interface defined in claim 1, further comprising a retainer ring mounted between the intersection of the ear module and the insert for securing the insert to the ear module.

9. The in-ear interface defined in claim 1, wherein the insert is glued to the ear module.

10. The in-ear interface defined in claim 1, wherein the insert is adapted to support acoustic equipment for sound transmission/emission through the sound bore.

11. The in-ear interface defined in claim 10, wherein the acoustic equipment has a receiver and a transmitter.

12. The in-ear interface defined in claim 11, further comprising filtering electronics between the receiver and the transmitter so as to filter sound for selective sound transmission through the in-ear interface.

13. The in-ear interface defined in claim 1, wherein the insert is shaped to snuggly fit within the cavity and the sound bore.

14. A method for customizing an in-ear interface in an ear of a person, comprising the steps of:
providing an ear module having an expandable body defining a cavity;
inserting at least partially an insert in the cavity of the ear module to generally maintain the shape of the cavity;
positioning a retainer device at the intersection of the insert and of the ear module, the retainer device contacting a portion of the ear module and a portion of the insert;
inserting the ear module in an ear of the person;
injecting a settable compound in the expandable body such that the ear module generally takes the shape of the ear;
removing the retainer device from the intersection of the insert and of the ear module;
removing the insert from the ear module upon curing of the settable compound so as to liberate the cavity of the ear module;
inserting acoustic equipment in the cavity of the ear module such that the equipment can transmit sound to the ear through the in-ear interface; and
reusing the retainer device at the intersection between the acoustic equipment and the ear module to retain the acoustic equipment in the ear module.

15. The method for customizing an in-ear interface defined in claim 14, further comprising the step of inserting at least partially the insert in a sound bore of the ear module.

16. The method for customizing an in-ear interface defined in claim 14, further comprising the step of reinserting the insert to the ear module following removal thereof, with acoustic equipment supported by the insert.

17. The method for customizing an in-ear interface defined in claim 14, further comprising the step of confirming an effectiveness of an acoustic seal between the ear module and the ear canal prior to connecting acoustic equipment to the insert.

18. The method for customizing an in-ear interface defined in claim 14, further comprising a step of measuring performance/physical attributes using a sound bore of the ear module.

* * * * *